United States Patent
Rankl et al.

(10) Patent No.: US 8,595,859 B1
(45) Date of Patent: Nov. 26, 2013

(54) CONTROLLING ATOMIC FORCE MICROSCOPE USING OPTICAL IMAGING

(75) Inventors: Christian Rankl, Linz (AT); Asger Iversen, Aalborg (DK); Tianwei Jing, Tempe, AZ (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/249,654

(22) Filed: Sep. 30, 2011

(51) Int. Cl.
*G01N 23/00* (2006.01)

(52) U.S. Cl.
CPC .................................. *G01N 23/00* (2013.01)
USPC .................................. 850/6; 850/33; 73/105

(58) Field of Classification Search
USPC ........................................ 850/6, 33; 73/105
See application file for complete search history.

(56) References Cited

U.S. PATENT DOCUMENTS

| 5,898,106 | A | * | 4/1999 | Babcock et al. | 73/105 |
| 5,986,381 | A | | 11/1999 | Hoen et al. | |
| 7,615,738 | B2 | * | 11/2009 | Kley | 250/234 |
| 8,368,017 | B2 | * | 2/2013 | Jahnke et al. | 250/306 |

OTHER PUBLICATIONS

Copending U.S. Appl. No. 12/890,894, filed Sep. 27, 2010.

* cited by examiner

*Primary Examiner* — Kiet T Nguyen

(57) ABSTRACT

A method for optically controlling an atomic force microscope (AFM) includes acquiring an optical image of a sample using an optical imaging device, identifying a feature of interest on the sample using the optical image, acquiring a high resolution AFM image of the sample using an AFM imaging device, the AFM imaging device comprising a cantilever having a tip, overlaying the AFM image with the optical image at the feature of interest, and positioning the probe tip over the feature of interest using the optical image.

18 Claims, 4 Drawing Sheets

CONTROLLING ATOMIC FORCE MICROSCOPE USING OPTICAL IMAGING

BACKGROUND

An atomic force microscope (AFM) is a comparatively high-resolution type of scanning probe microscope. With demonstrated resolution of fractions of a nanometer, AFMs promise resolution more than 1000 times greater than the optical diffraction limit.

Conventional AFMs include a microscale cantilever with a sharp tip (probe tip) at its end that is used to scan the surface of a specimen or sample. The cantilever is typically silicon or silicon nitride with a tip radius of curvature on the order of nanometers. When the probe tip is brought into contact with the sample surface, forces between the probe tip and the sample surface lead to a deflection of the cantilever. Typically, the deflection of the cantilevered probe tip is measured using a laser spot reflected from the top of the cantilever and onto an optical detector. Other methods that are used include optical interferometry and piezoresistive AFM cantilever sensing.

Another component of an AFM is an actuator, which maintains the angular deflection of the tip that scans the surface of the sample in contact-mode. Most AFM instruments use three orthonormal axes to image the sample. The first two axes (e.g., X and Y axes or a horizontal plane) are driven to raster-scan the surface area of the sample with respect to the probe tip with typical ranges of 100 μm in each direction. The third axis (e.g., Z axis or vertical direction) drives the probe tip orthogonally to the plane defined by the X and Y axes for tracking the topography of the surface.

Generally, the actuator for Z axis motion of the probe tip to maintain a near-constant deflection in contact-mode requires a comparatively smaller range of motion (e.g., approximately 1 μm (or less) to approximately 10 μm). However, as the requirement of scan speeds of AFMs increases, the actuator for Z axis motion must respond comparatively quickly to variations in the surface topography. In a contact-mode AFM, for example, a feedback loop is provided to maintain the probe tip in contact with a surface. The probe tip-sample interaction is regulated by the Z feedback loop, and the bandwidth of the Z feedback loop dictates how fast scanning can occur with the Z feedback loop remaining stable.

Some conventional AFM systems also provide optical viewing access to the sample surface in addition to the AFM imaging. The user of the AFM may employ the optical viewing access to control and expedite certain operations of the AFM. However, the user must perform tedious manual adjustment, and thus act as a feedback loop, to correct inaccuracies or variations between the AFM and optical viewing access. For example, when the user wants to perform AFM experiments at a certain position related to a feature of interest, inaccuracies of motorized stage movements must be corrected manually based on the optical image. Such inaccuracies and subsequent manual corrections inhibit automated measurements and slow the analysis process. Further, in conventional AFM systems, the user manually moves the probe tip to within at least a millimeter above the sample surface, and then very slowly moves the tip toward the sample surface to avoid of crashing the ultra-sharp probe tip into the sample. The time required for this manual approach process typically takes about 5 to 15 minutes.

There is a need therefore, for an AFM apparatus that overcomes at least the shortcoming of known AFM apparatuses described above.

SUMMARY

In a representative embodiment, a method for optically controlling an atomic force microscope (AFM) includes acquiring an optical image of a sample using an optical imaging device; identifying a feature of interest on the sample using the optical image; acquiring a high resolution AFM image of the sample using an AFM imaging device, the AFM imaging device comprising a cantilever having a tip; and overlaying the AFM image with the optical image at the feature of interest. The probe tip is positioned over the feature of interest using the optical image.

In another representative embodiment, a system includes an optical microscope, and AFM and a controller. The optical microscope is configured to obtain an optical image of a surface of a sample, the optical image including at least one feature of interest identified by a user. The AFM is configured to obtain an AFM image of the sample surface in a region of the at least one feature of interest, the AFM including a cantilever having a tip for scanning the sample surface. The controller is configured to overlay the AFM image with the optical image and to position the probe tip automatically over the feature of interest using the overlaid optical image.

In yet another representative embodiment, a method is provided for controlling an AFM apparatus, including an AFM imaging device for acquiring AFM images of a surface of a sample and an optical imaging device for acquiring optical images of the sample surface. The method includes reducing a distance between a probe tip of the AFM imaging device and the sample surface using a motorized stage, the probe tip having a known shape; acquiring optical images of the sample surface using the optical imaging device, focusing on the probe tip or in a vicinity of the probe tip; determining when one of the probe tip and the sample surface are in focus; and automatically slowing the motorized stage when the probe tip and the sample surface are determined to be the predetermined distance from one another.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DETAILED DESCRIPTION

In the following detailed description, for purposes of explanation and not limitation, representative embodiments disclosing specific details are set forth in order to provide a thorough understanding of the present teachings. Descriptions of known devices, materials and manufacturing methods may be omitted so as to avoid obscuring the description of the example embodiments. Nonetheless, such devices, materials and methods that are within the purview of one of ordinary skill in the art may be used in accordance with the representative embodiments.

It is to be understood that certain terminology defined herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a", "an" and "the" include both singular and plural referents, unless the context clearly dictates otherwise. Thus, for example, "a device" includes one device and plural devices.

As used in the specification and appended claims, and in addition to their ordinary meanings, the terms "substantial" or "substantially" mean to within acceptable limits or degree.

As used in the specification and the appended claims and in addition to its ordinary meaning, the term "approximately" means to within an acceptable limit or amount to one having ordinary skill in the art.

Generally, the various embodiments provide systems and method of using optical feedback and computer vision algorithms to perform positioning adjustment of a tip in relation to one or more features of interest on the surface of a sample, effectively removing the user from the positioning feedback loop. As will be readily appreciated by one of ordinary skill in the art, the present teachings are applicable to various types of AFMs, which may also be referred to as scanning force microscopes (SFMs). The AFM systems comprise many electrical and mechanical components, the discussion of which is outside the scope of the present teachings.

Figure 1:
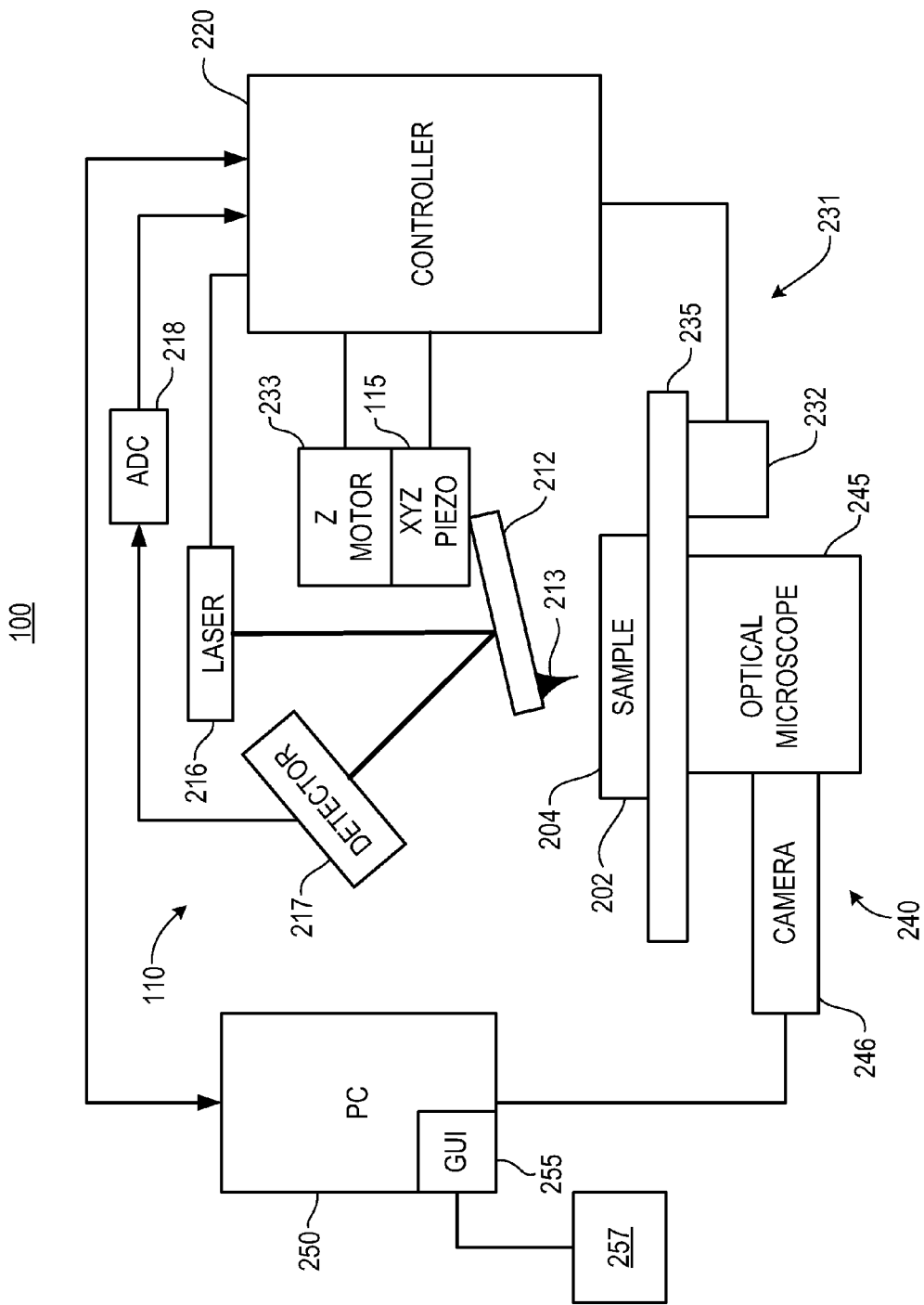
FIG. 1 is a simplified block diagram of an atomic force microscope (AFM) system, including an AFM and an optical microscope, in accordance with a representative embodiment.
Figure 2:
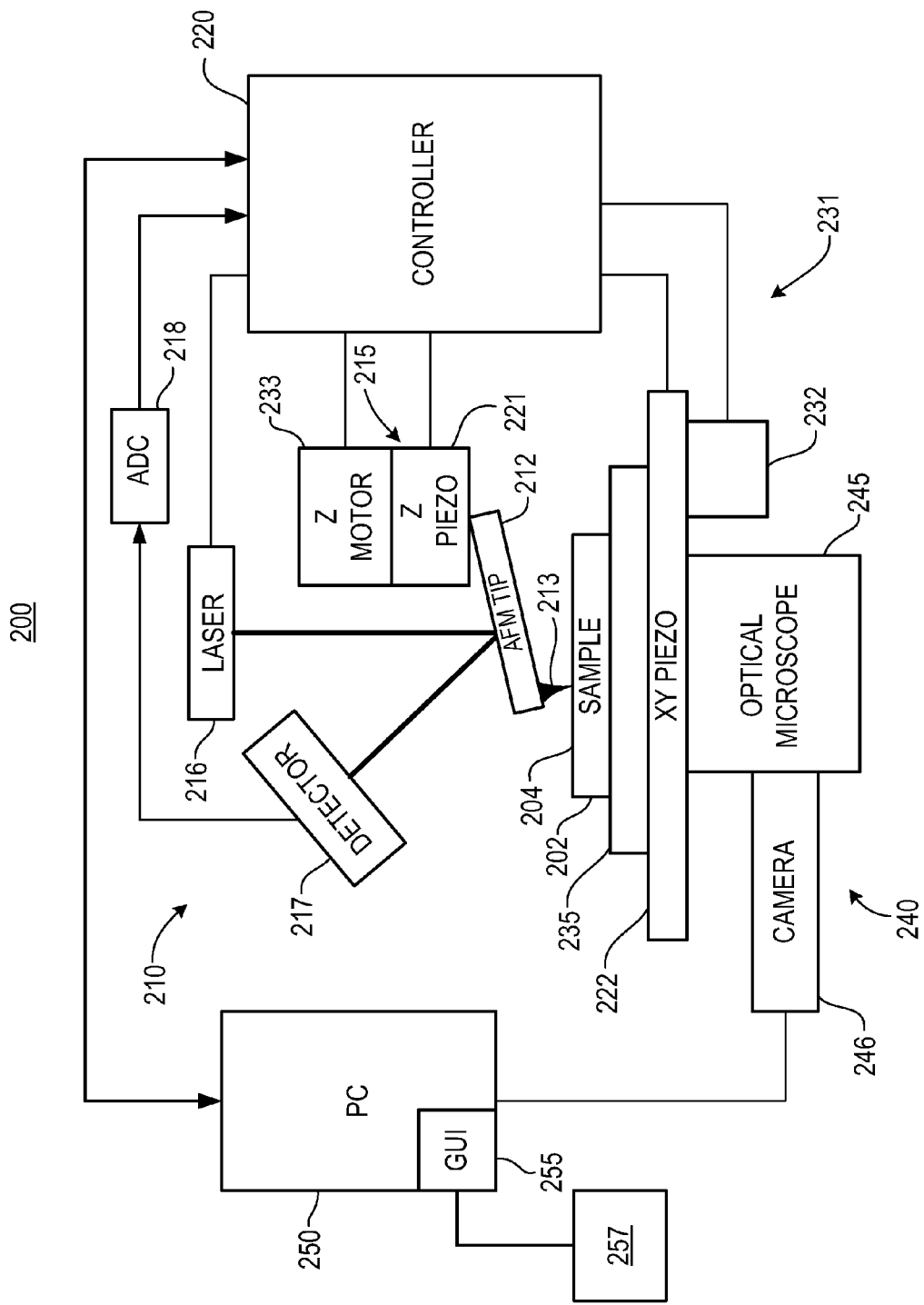
FIG. 2 is a simplified block diagram of an AFM system, including an AFM and an optical microscope, in accordance with another representative embodiment.

FIGS. 1 and 2 are simplified block diagrams of an AFM system, including an AFM and an optical microscope, in accordance with representative embodiments.

Referring to FIG. 1, AFM system 100 includes AFM imaging device 110, optical imaging device 240 and processing device 250. The AFM imaging device 110 acquires high resolution AFM images of sample 202, and generally includes a probe assembly and a motorized stage 231. The probe assembly includes a cantilever 212 with a probe tip 213 connected thereto, such that the probe tip 213 contacts a surface 204 of the sample 202 on base 235. An actuator 115 of the probe assembly is configured to make fine adjustments to the position of the probe tip 213 via the cantilever 212, while the motorized stage 231 is configured to make large adjustments to the position of the sample 202 in relation to the probe tip 213, under control of a controller 220. As described more fully herein, the sample 202 is generally moved in the X-Y plane of the coordinate system of FIG. 1 by the motorized stage 231 (i.e., x/y stage) and/or the actuator 115 to raster-scan the surface 204 of the sample 202, with the surface topography being mapped by motion of the probe tip 213 in the Z-direction.

The optical imaging device 240 acquires optical images of the sample 202, and generally includes optical microscope 245 and camera 246. The optical microscope 245 provides magnified visual images of the surface 204 of the sample 202, and provides the magnified visual images to the camera 246. The camera 246 records the images of the sample 202 in real-time, and provides digitized images to the processing device 250 for processing and/or storage. For example, the camera 246 may be a video camera capable of continuously recording the optical images, or a still photo camera configured to periodically capture the optical image, e.g., through operation of a shutter or other exposure mechanism.

The processing device 250 coordinates operations of the AFM imaging device 110 (via the controller 220) and the optical imaging device 240 in order to automatically and efficiently position the probe tip 213 over a feature of interest using the optical images from the optical imaging device 240 to accommodate acquiring the AFM images from the AFM imaging device 110. The processing device 250 includes a graphical user interface (GUI) 255 for interfacing with a user. For example, the GUI 255 may display on a display 257 the high resolution AFM images provided by the deflection detector 217 and the controller 220 and/or the optical images provided by the camera 246. For example, the AFM images and the optical images may be displayed overlaid on one another, as discussed below. The GUI 255 may also enable the processing device 250 to receive input from the user for various tasks, such as identifying one or more features of interest and/or defining a sequence of AFM experiments to be executed automatically at each of the identified features of interest. The coordinated operations of the AFM imaging device 110 and the optical imaging device 240 described herein may be referred to as Vision Control.

The motorized stage 231 of the AFM imaging device 110 may include motors, such as stepper motors, for example, corresponding to axes of motion for making large adjustments to the relative positioning between the probe tip 213 and the sample 202. In the embodiment depicted in FIG. 1, the motorized stage 231 includes first stage motor 232 connected to the base 235 and second stage motor 233 connected to the cantilever 212. The first stage motor 232 moves the position of the sample 202 horizontally beneath the probe tip 213 in the X-Y directions of the coordinate system indicated in FIG. 1, while the second stage motor 233 moves the position of the probe tip 213 vertically, via movement of the cantilever 212, in the Z direction. The first and second stage motors 232 and 233 are controlled by the controller 220 and the processing device 250 in order to automatically position the probe tip 213 substantially over the feature of interest, as discussed below with reference to FIG. 3. The first and second stage motors 232 and 233 alternatively may be controlled manually, for example, via the GUI 255 provided by the processing device 250.

The actuator 115 is configured to raise and lower the probe tip 213 vertically in the Z direction of the coordinate system shown in FIG. 1 in response to contact movement with the surface 204 of the sample 202 in order to maintain a substantially constant force between the probe tip 213 and surface 204 of the sample 202. The actuator 115 is further configured to adjust the probe tip 213 horizontally in the X-Y directions in order to establish and/or maintain the position of the probe tip 213 over a feature of interest on the surface 204 of the sample 202. The actuator 115 may be a piezoelectric actuator, for example, although other types of actuators may be incorporated without departing from the scope of the present teachings. In the embodiment depicted in FIG. 1, the actuator 115 makes all adjustments to the relative positioning of the probe tip 213 with respect to the sample 202 by moving the cantilever 212 in response to control signals from the controller 220. More particularly, the actuator 115 is controlled by the controller 220 and the processing device 250 to precisely position the probe tip 213 over the feature of interest automatically, as discussed below with reference to FIG. 3. The actuator 115 may also be controlled by the controller 220 and the processing device 250 to efficiently approach the probe tip 213 to the surface 204 of the sample 202 at the feature of interest automatically, as discussed below with reference to FIG. 4. The controller 220 illustratively includes a proportional-integral-differential (PID) filter block and a series of digital biquadratic filters, known to one of ordinary skill in the art.

The probe tip 213 and cantilever 212 may be monolithically formed from a common substrate using known semiconductor processing techniques, and fastened to the actuator 115. Alternatively, the cantilever 212, the probe tip 213 and at least a portion of the actuator 115 may be monolithically formed from a common substrate. In representative embodiments, the probe tip 213 is configured to contact the surface 204 of the sample 202 in order to make measurements of the surface topography, and thus the AFM system 100 may be referred to as a contact-mode AFM. An example of a piezoelectric actuator is described in commonly owned U.S. patent application Ser. No. 12/890,894, filed on Sep. 27, 2010, and published as U.S. Patent Application Pub. No. 2012/0079634 on Mar. 29, 2012, entitled "Tandem Piezoelectric Actuator and Single Drive Circuit for Atomic Force Microscopy," to D. Schroeder, et al., the disclosure of which is hereby incorporated by reference. An example of an actuator other than a piezoelectric actuator is an electrostatic "nanostepper" actuator, such as described in commonly owned U.S. Pat. No. 5,986,381 to S. Hoen et al., dated Nov. 16, 1999, entitled "Electrostatic Actuator with Spatially Alternating Voltage Patterns," the disclosure of which is hereby incorporated by reference.

The AFM system 100 further includes a laser 216 (or other suitable light source) disposed above the surface 204 of the sample 202. The laser 216 directs light (laser spot) which is reflected at the cantilever 212 and is incident on a deflection detector 217. The deflection detector 217 provides a deflection signal to an analog-to-digital converter (ADC) 218, which provides a digitized signal to the controller 220 to provide a feedback loop. The deflection signal is indicative of the vertical movement of the probe tip 213. In response to the deflection signal, the controller 220 provides output signals to the actuator 115 and/or the second stage motor 233 of the motorized stage 231 via digital-to-analog converters (DACs) (not shown). The cantilever 212 and probe tip 213 are thus raised and lowered to maintain a constant deflection equal to a predetermined setpoint deflection, leading to a constant force between the probe tip 213 and the surface 204 of the sample 202 in contact-mode.

Referring to FIG. 2, AFM system 200 similarly includes AFM imaging device 210, optical imaging device 240 and processing device 250. The AFM imaging device 210 generally includes the probe assembly and the motorized stage 231. The optical imaging device 240, the processing device 250 and the motorized stage 231 are substantially the same as discussed above with reference to FIG. 1, and thus the corresponding descriptions will not be repeated.

The probe assembly includes the cantilever 212 with probe tip 213 connected thereto, such that the probe tip 213 contacts the surface 204 of the sample 202 on base 235, similar to the discussion above of the probe assembly. The probe assembly also includes actuator 215 for fine tuning the relative position of the probe tip 213 and the sample 202. However, unlike the actuator 115 in FIG. 1, the actuator 215 is implemented in separate locations. More particularly, in the representative embodiment depicted in FIG. 2, the actuator 215 includes first piezoelectric stage 221 connected to the cantilever 212 for vertically adjusting the probe tip 213 in the in the Z-direction of the coordinate system shown in FIG. 2 in response to control signals from the controller 220. The actuator 215 further includes second piezoelectric stage 222 connected to the base 235 for horizontally adjusting the position of the sample 202 in relation to the probe tip 213 in the X-Y directions in response to control signals from the controller 220. In the configuration depicted in FIG. 2, the position of the probe tip 213 is fixed with respect to the optics. This enables performance of various advanced optical techniques, such as probe tip enhanced raman spectroscopy, simultaneously with AFM imaging. In addition, movements in the X-Y directions are clearly uncorrelated with movements in the Z directions.

In FIGS. 1 and 2, each of the controller 220 and the processing device 250 may be implemented in whole or in part by a computer processor, such as a microprocessor or central processing unit (CPU), application specific integrated circuits (ASICs), field-programmable gate arrays (FPGAs), or combinations thereof, using software, firmware, hard-wired logic circuits, or combinations thereof. In an embodiment, the controller 220 may include an FPGA onto which very high speed integrated circuit hardware description language (VHDL) code has been compiled and uploaded, and the processing device 250 may include a personal computer (PC) controlled by an operating system, for example. However, it is understood that the controller 220 and the processing device 250 may be implemented by various alternative means, without departing from the scope of the present teachings. For example, all or part of the functionality of the controller 220 may be included in the processing device 250, or vice versa. Also, one or both of the controller 220 and the processing device 250 may be a real-time operating system used in the AFM system 100, 200 or as a standalone device.

When the controller 220 or the processing device 250 uses a processor or CPU, a memory (not shown) is included for storing executable software/firmware and/or executable code that controls the signals to the actuator 115, 215 and/or the first and second stage motors 232 and 233, for example. The memory may be any number, type and combination of non-volatile read only memory (ROM) and volatile random access memory (RAM), and may store various types of information, such as computer programs and software algorithms executable by the processor or CPU. The memory may include any number, type and combination of tangible computer readable storage media, such as a disk drive, an electrically programmable read-only memory (EPROM), an electrically erasable and programmable read only memory (EEPROM), a CD, a DVD, a universal serial bus (USB) drive, and the like.

Figure 3:
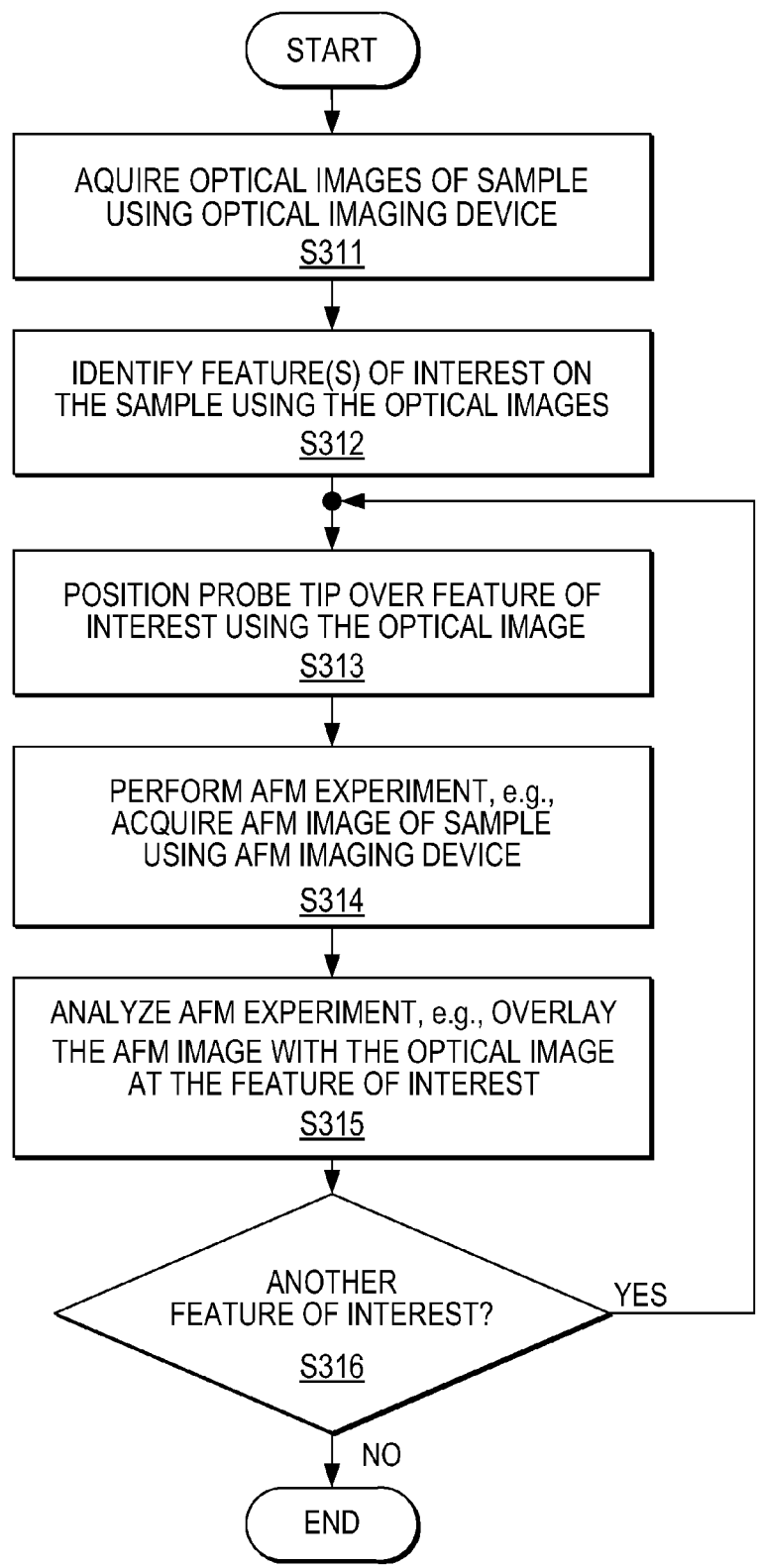
FIG. 3 is a flow diagram showing automatic optical control of an AFM system in accordance with a representative embodiment.

FIG. 3 is a flow diagram showing automatic optical control of an AFM system in accordance with a representative embodiment, e.g., using the AFM system 100 or 200, discussed above. The operations of FIG. 3 may be executed by the processing device 250, the controller 220, or a combination of both.

Referring to FIG. 3, an optical image of surface 204 of the sample 202 is acquired using optical imaging device 240 in block S311. In an embodiment, the optical image is acquired by the optical microscope 245 and the camera 246, which provides the optical image to the processing device 250. In alternative embodiments, the optical microscope 245 may be replaced with a different optical access, which is less powerful than the optical microscope 245, but sufficient to provide a usable optical image to the processing device 250.

In block S312, one or more features of interest are identified on the sample surface 204 using the optical image. The features of interest may be identified using any feature identification technique, without departing from the scope of the present teachings. For example, the processing device 250 may execute an edge detection algorithm to identify one or more patterns on the optical image provided by the camera 246. The edge detection algorithm may be performed automatically, where various features of interest are identified across the sample surface 204 in response to predetermined patterns identified through edge detection. Alternatively, the features of interest may be identified using specific coordinates (e.g., in the X-Y plane) on the optical image, where the coordinates may be entered by the user via the GUI 255. For example, the GUI 255 may enable the user to position a visual indicator (such as an X or a dot) on the optical image displayed on the display 257 using a mouse, a keyboard or other interface device, where the indicated position corresponds to the feature of interest. The processing device 250 translates the indicated position into corresponding physical coordinates on the optical image (and thus on the sample surface 204). In this manner, the location corresponds to the feature of interest, independent of the particular visual feature or pattern that may appear on the sample surface 204 at that location.

In block S313, the probe tip 213 is positioned over one of the features of interest using the optical image acquired by the optical imaging device 240. Positioning the probe tip 213 may be implemented in a multiple step process. For example, once the location of the feature of interest is known (e.g., by the processing device 250 determining the physical coordinates of the same), relatively large movements of the probe tip 213 are initially performed by the motorized stage 231 under control of the controller 220. That is, the first stage motor 232 moves the base 235 horizontally to position the sample 202 relative to the probe tip 213 in the X-Y plane, and the second stage motor 233 moves the cantilever 212 vertically to position the probe tip 213 in the Z-direction. Operation of the motorized stage 231 is able to move the probe tip 213 with respect to the feature of interest within a range of approximately 3 µm to approximately 4 µm, for example, and may position the probe tip 213 within approximately 500 µm vertically above the feature of interest (as discussed further below).

Relatively smaller adjusting movements (fine-tuning) of the probe tip 213 are then performed by the actuator 115, 215 under control of the controller 220. That is, referring to FIG. 1, the actuator 115 adjusts the cantilever 212 vertically and horizontally to position the probe tip 213 in the X, Y and Z directions. Referring to FIG. 2, the first piezoelectric stage 221 adjusts the cantilever 212 vertically to position the probe tip 213 in the Z direction and the second piezoelectric stage 222 adjusts the base 235 horizontally to position the sample 202 relative to the probe tip 213 in the X-Y plane. The actuators 115, 215 are able to adjust the relative positioning of the probe tip 213 with respect to the feature of interest within a range of approximately 0.18 µm to approximately 0.36 µm, for example.

The large and small movements of the probe tip 213 are based, at least in part, on analysis of the optical image by the processing device 250 and feedback to the controller 220. The analysis includes comparing the actual position of the probe tip 213 with a target position of the probe tip 213 corresponding to the identified feature of interest. The analysis of the optical image may be feature based or pixel based, for example, although other analysis techniques may be incorporated without departing from the scope of the present teachings. In a feature based analysis, measurements between the actual and target positions of the probe tip 213 may be made by detecting features in the optical image of the actual position and the distance from each of the detected features to the target position is measured. In a pixel based analysis, measurements between the actual and target positions of the probe tip 213 are made between pixels corresponding to the feature of interest on the optical image.

In block S314, an AFM experiment is performed with respect the feature of interest over which the probe tip 213 has been positioned. For example, an AFM image of the sample surface 204 may be acquired using AFM imaging device 110, 210. The AFM image may be acquired in a know manner. For example, the laser 216 directs a laser spot to the back of the cantilever 212, which reflects the laser spot to the deflection detector 217. The deflection detector 217 provides a deflection signal to the ADC 218, which provides a digitized signal to the controller 220. The deflection signal indicates corresponding features of the sample surface 204.

The results of the AFM experiment are then analyzed in block S315. For example, the high resolution AFM image may be overlaid with the optical image in the region of the feature of interest. Overlaying the high resolution AFM image with the optical image at the feature of interest may be performed automatically by the processing device 250 using feature recognition via an edge detection algorithm, for example, in order to correctly align the AFM and optical images. However, overlaying the AFM and optical images may involve other alignment techniques, without departing from the scope of the present teachings, such as correlation and tracking techniques, either alone or in some combination of techniques. Correlation generally includes mapping physical coordinates from the optical image to physical coordinates of the AFM image in the region of the feature of interest. The mapping may include direct pixel correlation, in which pixels of the optical image are mapped to corresponding pixels of the AFM image. The mapping may also include feature recognition, in which detected features (e.g., edges) are correlated to the position of the feature of interest on the AFM image. Tracking techniques may include template based tracking, for example, in which the processing device 250 saves templates and then locates the saved templates in tracked optical images, e.g., using normalized cross-correlation as well as a prediction of where they are going to be, to improve performance. Kinds of descriptors other than templates may be used, although simple image templates are very fast and precise under the right conditions.

Generally, overlaying the AFM image with the optical image reveals details of topographical, mechanical and/or electrical properties at the feature of interest. For example, a particular visual pattern on the optical image may be matched with height determinations provided by the AFM image to provide topographical data corresponding to the visual pattern, thus providing a more complete representation of the surface 204 of the sample 202. Further, in an embodiment, overlaying the AFM image with the optical image may further include applying an affine transformation to correct for stretching, rotation, shifting and/or shearing between the optical image and the AFM image.

Once the alignment is established, the processing device 250 is able to access movement in the optical image through the camera 246. The processing device 250 converts the accessed movement to physical coordinates, and may correct distortions of the optical image using the physical coordinates. Notably, alignment is not necessarily required to access movement in the optical image, and the transformation between the optical image and physical coordinates may be estimated using pixel size of the camera 246 and magnification of the optical microscope 245. However, the alignment may be used to access physical coordinates with higher precision and in systems where the pixel size of the camera 246 and/or the magnification of the optical microscope 245 is unknown.

In addition, feedback from the optical image provided by the optical imaging device 240 may be used to automatically align a laser spot from the laser 216 on the cantilever 212. For example, the cantilever 212 may be detected by the optical microscope 245 (with the sample 202 not present) and the processing device 250 using black and white pattern recognition for speed. By recognizing the cantilever 212, the processor is able to determine the current position of the cantilever and to adjust the laser spot automatically to a predefined position on the backside of the cantilever 212 by moving the physical position of the laser 216 via the controller 220.

In block S316, it is determined whether any additional features of interest have been identified, e.g., in block S312. If so (block S316: Yes), then the process returns to block S313 to position the probe tip 213 over the additional feature of interest using the optical image. The process described with reference to blocks S314-S316 may then be repeated. If no additional features of interest have been identified (block S316: No), then the process ends. Notably, the order of the blocks in FIG. 3 may vary without departing from the scope of the present teachings. For example, the features of interest may be identified (e.g., block S312) one at a time, and thus the determination of whether another feature of interest has been identified (e.g., block S316) may be made after block S312.

Figure 4:
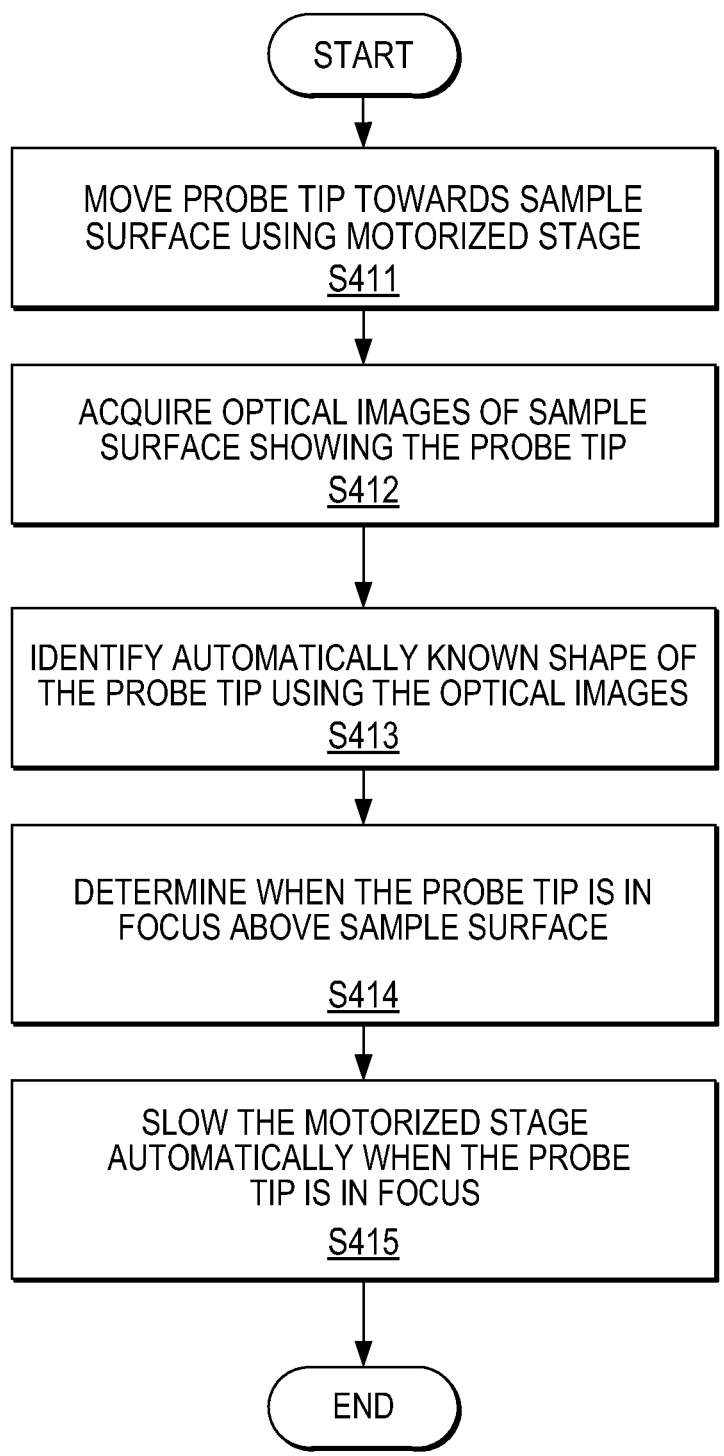
FIG. 4 is a flow diagram showing automatic optical control of an AFM system in accordance with a representative embodiment.

FIG. 4 is a flow diagram showing automatic optical control of an AFM system in accordance with another representative embodiment, in which a probe tip of an AFM imaging device is automatically and quickly driven from a safe location above a sample surface into contact by the motorized state of the AFM imaging device, without user manipulation. The operations of FIG. 4 may be executed by the processing device 250, the controller 220, or a combination of both.

Referring to FIG. 4, the distance between the probe tip 213 of the AFM imaging device 210 and the surface 204 of sample 202 is reduced under control of the processing device 250 and the controller 220. More particularly, in block S411, the probe tip 213 is moved vertically towards the surface of sample 202 using the motorized stage 231. In block S412, the optical imaging device 240 acquires optical images of the surface 204 of the sample 202 while the probe tip 230 is moved toward the surface 204 of the sample 202, where the optical images show the probe tip 213. The optical images are captured by the camera 246 and provided to the processing device 250.

The probe tip 213 has a shape known by the processing device 250, enabling comparison of the shape of the probe tip 213 with shapes appearing in the optical image. Thus, in block S413, the processing device 250 automatically identifies the known shape of the probe tip 213 in the optical images. For example, the processing device 250 may be programmed with dimensions of the probe tip 213, or a database of probe tip dimensions may be stored on a computer readable storage medium so that the processing device 250 is able to look up the dimensions of the probe tip 213 based on identification information entered by the user via the GUI 255. Alternatively, the processing device 250 may be calibrated using an actual image of the probe tip 213 obtained by the optical imaging device.

In block S414, the processing device 250 determines when the probe tip 213 is in focus above the surface 204 of the sample 202 based on the identified known shape of the probe tip 213 in the optical images. Alternatively, a known autofocus algorithm, such as summing the gradient image or edge detection, may be used to determine when the probe tip 213 is focus. The processing device 250 automatically causes the motorized stage 231 to slow when the probe tip is in focus in block S415. In this manner, the probe tip 213 can be automatically positioned vertically above the sample 202 within approximately 15 μm of the surface 204 of the sample 202 in less than one minute, for example. From this position, the processing device 250 is able to carefully contact the probe tip 213 to the surface 204 of the sample 202 automatically and quickly, through control of the actuator 115, 215 via the controller 220, using a known surface approach algorithm, for example, stopping until the force acting on cantilever 212 exceeds a certain threshold. This automated process reduces the time for getting the probe tip 213 into contact with the surface 204 of the sample 202, increases the accuracy of positioning the probe tip 213 very close to the surface 204 of the sample 202, and otherwise avoids the risk of accidentally crashing the probe tip 213 into the sample 202.

In an alternative embodiment, the distance between the probe tip 213 of the AFM imaging device 210 and the surface 204 of the sample 202 is reduced by moving the sample 202 vertically towards the probe tip 213, while the probe tip 213 remains stationary, using the motorized stage 231 under control of the processing device 250 and the controller 220, where the probe tip 213 has a known shape. The optical imaging device 240 acquires optical images of the surface 204 of the sample 202 while the sample 202 is moved toward the probe tip 213, where the optical imaging device focuses at the probe tip 213 or in the vicinity of the probe tip 213. The optical images are captured by the camera 246 and provided to the processing device 250. The processing device 250 is able to automatically determine when the surface 204 of the sample 202 is in focus (or nearly in focus) under the probe tip 213, for example, based on identified sharpness and/or known features in the optical images. To identify the sharpness, for example, the optical imaging device may have short depth of field (e.g., less than about 100 μm). The processing device 250 then automatically causes the motorized stage 231 to slow when the surface 204 of the sample 202 is in focus or nearly in focus, indicating close proximity of the surface 204 and the probe tip 213.

In this manner, the sample 202 can be automatically positioned vertically under the probe tip 213 within approximately 15 μm in less than one minute, for example. From this position, the processing device 250 is able to carefully contact the probe tip 213 and the surface 204 of the sample 202 automatically and quickly, through control of the actuator 115, 215 via the controller 220, using a known surface approach algorithm, for example. Of course, in alternative embodiments, the distance between the probe tip 213 of the AFM imaging device 210 and the surface 204 of the sample 202 may be reduced according to various combinations of moving the probe tip 213 and the sample 202.

Accordingly, the various embodiments enable protocols for performing AFM measurements to be automated. By using Vision Control optical feedback to position the probe tip 213 to a desired location of the feature of interest, error caused by movement inaccuracies the first and second stage motors 232 and 233, for example, is eliminated. In other words, the probe tip 213 is substantially perfectly aligned with the feature of interest optically. The automation and control enables implementation of automated workflows. For example, the user can pre-select multiple features of interest on the surface 204 of the sample 202 (e.g., in block 5312 of FIG. 3) and define a sequence of AFM experiments to be executed at each of the features of interest. According to various embodiments, the processing device 250 is able to systematically and automatically locate each of the features of interest and to execute the one or more AFM experiments at each. The AFM experiments may include, for example, acquiring an AFM image of the feature of interest, imaging the area around the feature of interest, performing force distance cycles to calculate properties such as elasticity, and/or measuring electrical properties of the feature of interest.

Furthermore, the various embodiments use existing optics (e.g., optical imaging device 240) already included in the AFM system 100, 200, so no additional cost incurred. In comparison, other closed loop feedback position control techniques rely on encoders and positioning sensors, which typically cost thousands of dollars.

In view of this disclosure it is noted that the various apparatuses and methods for controlling an AFM can be implemented in variant structures, using variant components and variant methods in keeping with the present teachings. Further, the various components, structures and parameters are included by way of illustration and example only and not in any limiting sense. In view of this disclosure, those skilled in the art can implement the present teachings in determining their own applications and needed components, materials, structures and equipment to implement these applications, while remaining within the scope of the appended claims.

The invention claimed is:

1. A method for optically controlling an atomic force microscope (AFM), the method comprising:
   acquiring an optical image of a sample using an optical imaging device;
   identifying a feature of interest on the sample using an automatic feature recognition technique on the optical image;
   acquiring a high resolution AFM image of the sample using an AFM imaging device, the AFM imaging device comprising a cantilever having a tip;
   overlaying the AFM image with the optical image at the feature of interest; and
   positioning the tip over the feature of interest using the optical image.

2. The method of claim 1, further comprising:
   aligning the optical image and the AFM image;
   accessing movement in the optical image; and
   converting the movement to physical coordinates for correcting distortions of the optical image.

3. The method of claim 1, wherein identifying the feature of interest comprises performing edge detection on the optical image.

4. The method of claim 1, wherein overlaying the high resolution AFM image with the optical image at the feature of interest is performed automatically using at least one of feature recognition, correlation and tracking techniques.

5. The method of claim 1, wherein positioning the tip over the feature of interest comprises:
   initially performing large movements of the tip using a motorized x/y stage; and
   performing smaller movements of the tip using a piezoelectric stage based on analysis of the optical image, the analysis comprising comparing an actual position of the tip with a target position of the tip corresponding to the identified feature of interest.

6. The method of claim 5, wherein the analysis of the optical image is at least one of feature based and pixel based.

7. The method of claim 1, wherein positioning the tip over the feature of interest comprises moving the sample in relation to the tip.

8. The method of claim 1, wherein positioning the tip over the feature of interest comprises moving the tip in relation to the sample.

9. The method of claim 1, wherein overlaying the AFM image with the optical image comprises mapping coordinates of the optical image to coordinates of the AFM image using one of direct pixel correlation and feature recognition.

10. The method of claim 9, wherein overlaying the AFM image with the optical image further comprises applying an affine transformation to correct for at least one of stretching, rotation, shifting and shearing between the optical image and the AFM image.

11. The method of claim 1, further comprising:
    identifying at least one additional feature of interest on the sample using the optical image; and
    defining a sequence of AFM experiments to be executed at each of the identified features of interest.

12. A method for optically controlling an atomic force microscope (AFM), the method comprising:
    acquiring an optical image of a sample using an optical imaging device;
    identifying a feature of interest on the sample using the optical image;
    acquiring a high resolution AFM image of the sample using an AFM imaging device, the AFM imaging device comprising a cantilever having a tip;
    overlaying the AFM image with the optical image at the feature of interest;
    positioning the tip over the feature of interest using the optical image; and
    automatically aligning a laser spot with a predefined position on the cantilever based on the optical image by detecting the cantilever using pattern recognition on the optical image using the optical imaging device.

13. The method of claim 12, wherein the pattern recognition comprises black and white pattern recognition.

14. A system, comprising:
    an optical microscope configured to obtain an optical image of a surface of a sample, the optical image including at least one feature of interest identified by a user;
    an atomic force microscope (AFM) configured to obtain an AFM image of the sample surface in a region of the at least one feature of interest, the AFM comprising a cantilever having a tip for scanning the sample surface;
    a controller configured to overlay the AFM image with the optical image and to position the tip automatically over the feature of interest using the overlaid optical image;
    a laser configured to direct a laser spot to a predefined position on the cantilever, which reflects the laser spot; and
    a deflection detector configured to generate a deflection signal, provided to the controller, in response to the reflected laser spot, the deflection signal indicating corresponding features of the sample surface.

15. The system of claim 14, wherein the controller overlays the AFM image with the optical image at the feature of interest automatically using at least one of feature recognition, correlation and tracking techniques.

16. The system of claim 14, wherein the controller overlays the AFM image by mapping coordinates of the optical image to coordinates of the AFM image using one of direct pixel correlation and feature recognition.

17. The system of claim 14, wherein the laser spot is automatically aligned with the predefined position on the cantilever based on the optical image by detecting the cantilever using pattern recognition on the optical image.

18. The system of claim 17, wherein the pattern recognition comprises black and white pattern recognition.

* * * * *